United States Patent [19]

Tofsrud

[11] Patent Number: 5,704,575
[45] Date of Patent: Jan. 6, 1998

[54] PATIENT SUPPORT DEVICE

[76] Inventor: Duane Tofsrud, 1915 Arcade St., Apt. 105, Maplewood, Minn. 55109

[21] Appl. No.: 552,787

[22] Filed: Nov. 3, 1995

[51] Int. Cl.⁶ .................................................. F16M 11/00
[52] U.S. Cl. .......................................................... 248/200
[58] Field of Search ................................. 248/250, 251, 248/222.52, 222.41, 447.1; 211/104, 105.1; 378/177, 179, 208; 5/601; 297/195.11

[56] References Cited

U.S. PATENT DOCUMENTS

| | | | |
|---|---|---|---|
| 2,552,592 | 5/1951 | Rush | 5/601 X |
| 4,223,862 | 9/1980 | Doughty | 248/222.52 |
| 4,696,025 | 9/1987 | Taylor | 378/177 X |
| 5,415,299 | 5/1995 | Usner | 211/105.1 |

*Primary Examiner*—Ramon O. Ramirez
*Attorney, Agent, or Firm*—Jacobson & Johnson

[57] ABSTRACT

A patient support device having a base member and an upright member for a patient to grasp, with the upright member pivotally carried by the base member to permit the upright member to be moved from a collapsed and out-of-the-way position to an extended position where a patient can grasp the upright member for support while an x-ray is being taken of the patient.

9 Claims, 3 Drawing Sheets

PATIENT SUPPORT DEVICE

FIELD OF THE INVENTION

This invention relates generally to patient support devices and more specifically, to patient support devices for use while the patient is being x-rayed.

BACKGROUND OF THE INVENTION

One of the difficulties of taking x-rays of people as they stand is the difficultly an older, ill or injured patient has to remain still while the x-ray is being taken. In order to assist the patient in remaining still, some type of support is used. One type of prior art patient support device comprises a bar that extends laterally outward from the wall which the patient may grasp for support. Other items such as chair or i.v stands might also be used to support the patient. The present invention provides an improved patient support device that reduces radiation exposure to the staff and can be quickly and easily moved to an out-of-the-way position when not in use.

BRIEF DESCRIPTION OF THE PRIOR ART

U.S. Pat. No. 4,223,862 shows a patient support apparatus with a patient holding bar that can be positioned horizontally to permit a patient to grasp the bar while an x-ray is being taken of the patient.

SUMMARY OF THE INVENTION

Briefly, the invention comprises a patient support device having a base member and an upright member for a patient to grasp with the upright member pivotally carried by the base member to permit the upright member to be moved from a collapsed and out-of-the-way position to an extended position where a patient can grasp the upright member for support while an x-ray is being taken of the patient.

DESCRIPTION OF THE PREFERRED EMBODIMENT

Figure 1:
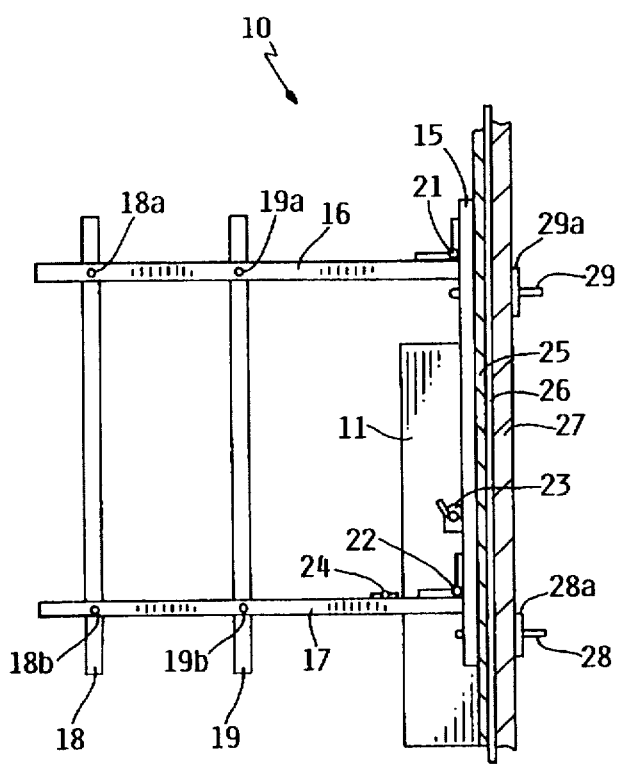
FIG. 1 shows a side view of the patient support device mounted to a wall.

Referring to FIG. 1 reference numeral 10 identifies my patient support device. The patient support device includes a base member 15 for attachment to a wall comprised of sheet rock 25, screening 26, and reinforcing member 27. A first toggle bolt 29 and a second toggle bolt 28 extend through base member 15 to hold base member 15 in position.

The patient support device 10 includes an upper elongated support bar 16 extending laterally outward with a first end hingedly mounted to base member 15 through a butt hinge 21. Similarly, a lower elongated support bar 17 extends laterally outward and parallel to a support bar 16. One end of support bar 16 includes a first end hingedly mounted to base member 15 through butt hinge 21. Extending transversely to members 16 and 17 is a first upright member 18 having a first end pivotally connected to first elongated support bar 16 through a pivot member 18a and a second end pivotally connected to support bar 17 through pivot member 18b. Similarly, extending transversely to members 16 and 17 is a second upright member 19 having a first end pivotally connected to first elongated support bar 16 through a pivot member 19a and a second end pivotally connected to support bar 17 through pivot member 19b. Members 16, 17, 18, and 19 are preferably made of a hard wood such as oak and have a diameter which is sufficiently large enough to permit comfortable grasping by patients to enable the patients to steady themselves as an x-ray is being taken.

Located on base member 15 is a latch mechanism 23 and located on lower elongated support bar 17 is a bolt for engagement with latch 23. Extending behind the patient support device is an x-ray unit 11.

Figure 2:
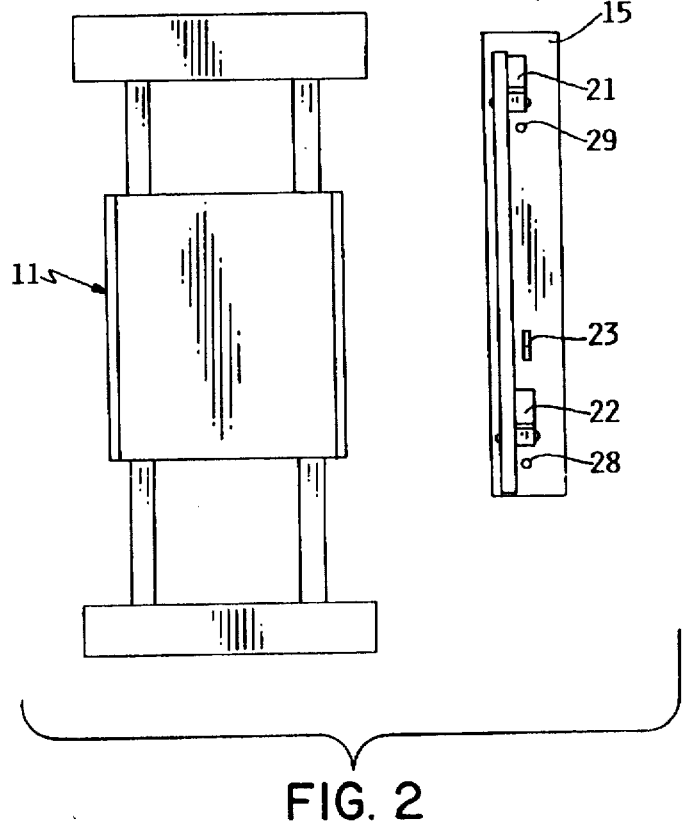
FIG. 2 shows a front view of my patient support device positioned proximate to an x-ray machine.

FIG. 2 shows x-ray unit 11 position adjacent to patient support device 10. In this condition, the patient can stand in front of x-ray devices and reach out and grasp the patient support device 10 to steady the person while the x-ray is being taken.

Figure 3:
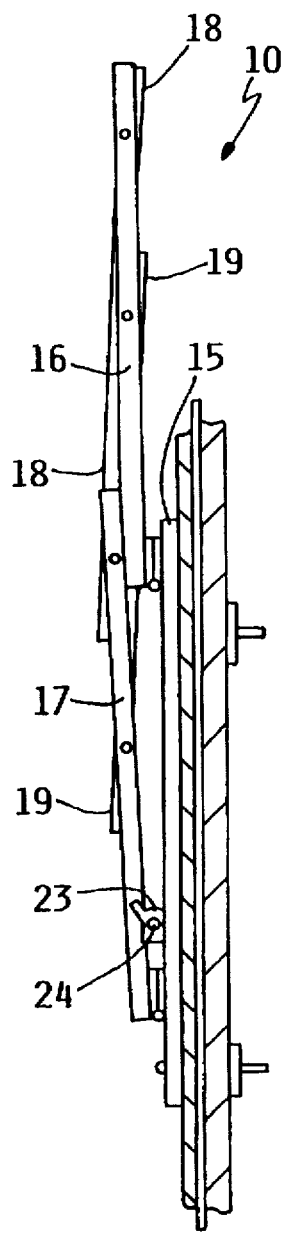
FIG. 3 show a side view of the patient support device in a collapsed and out-of-the-way position.

FIG. 3 shows the collapsible nature of my invention which permits the patient support device 10 to be moved to an out-of-the-way position. In the out-of-the-way position shown in FIG. 2, the support bar 16 and lower elongated support bar 17 are folded upward through hinges 21 and 22. The pivotal members 18a and 18b which hold member 18 to support bar 16 and lower elongated support bar 17 and the members 18a and 18b which hold member 18 to support bar 16 and lower elongated support bar 17 in pivotal relationship. By rotating lower elongated support bar 17 clockwise all the members 18, 19, 16 and 17 move together and collapse on each other until they are in the position shown in FIG. 3. In this condition the latch 23 engages pin 24 to hold the patient support device 10 in an out-of-the-way position.

Figure 4:
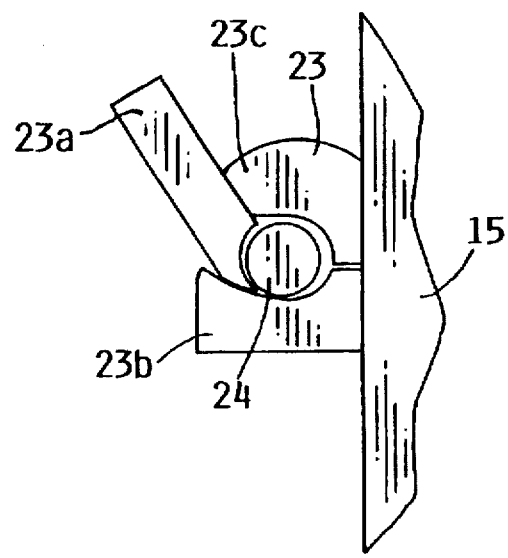
FIG. 4 shows the latch mechanism for holding the patient support device in an out-of-the-way position.

FIG. 4 shows a detail of the latch mechanism 23 and pin 24 for holding the unit in position. Latch mechanism 23 is a conventional gate latch mechanism that includes a pivot member 23a which engages pin 24 on member 17 to hold the pin 24 in position. To release the gate latch mechanism 23 is released through a mechanism (not shown) to allow the member 24 to clear the latch mechanism jaws 23b and 23c.

Figure 5:
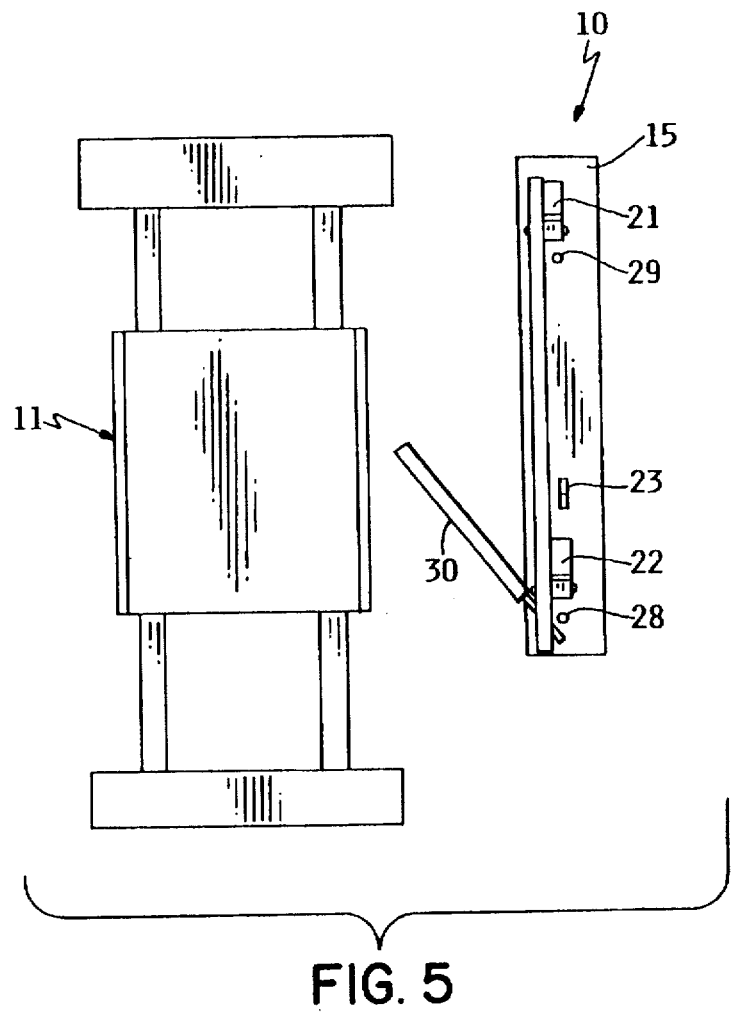
FIG. 5 shows an alternate embodiment with an angled support for smaller patients.

FIG. 5 shows an alternate embodiment with an additional patient grasp bar 30 that angles outward from patient support device 10. The purpose of the angled patient support is to provide an angled bar for use with children who may have shorter arms. That is, the patient can still be in front of x-ray unit 11 and grasp onto grasp bar 30 as grasp bar 30 is closer to the x-ray unit than the vertical members 18 or 19.

Figure 6:
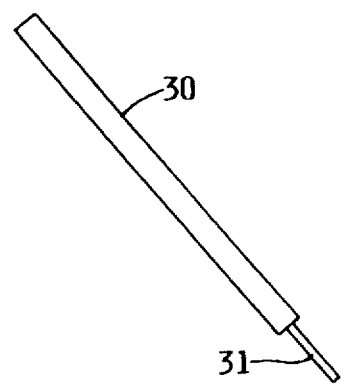
FIG. 6 shows the angled support.

FIG. 6 shows an isolated view of patient grasp bar 30 with a bolt 31 extending from one end of bar 30. The bolt is inserted through an opening in member 19 and to hold patient support bar 30 in the angled position shown in FIG. 5.

In operation of the unit the patient has a choice of which portion of the support is grasped. That is, the patient can steady himself or herself on the horizontal members 16 and 17 or the vertical members 18 and 19.

While the invention is shown with a single hinge for folding upward the unit, in certain instances one may want to place additional hinges to allow for double folding of members 16 and 17. This would permit folding of the unit where there is less overhead clearance.

I claim:

1. A patient support device comprising:
   a base member for attachment to a wall;
   a first elongated support bar, said first elongated bar having a first end hingedly mounted to said base member;
   a second elongated support bar, said second elongated support bar having a first end hingedly mounted to said base member;
   an upright member, said upright member having a first end pivotally connected to said first elongated support bar and a second end pivotally connected to said second elongated member with said first elongated support bar and said second elongated support bar normally projecting laterally outward from said base member to enable a patient to grasp the elongated support bars or the upright members to stabilize the patient while an x-ray is being taken.

2. The patient support device of claim 1 including:
   a second upright member pivotally connected to said first elongated member and said second elongated member.

3. The patient support device of claim 2 wherein the upright members and elongated support bars are made of wood.

4. The patient support device of claim 2 wherein the upright members are sufficiently long to extend past the elongated support bar.

5. The patient support device of claim 4 wherein the base member includes toggle bolts for securing to a wall.

6. The patient support device of claim 4 including a latch for holding said support device in a folded condition proximate the base member.

7. The patient support device of claim 4 including a further upright member, said further upright member angled mounted with respect to said upright members.

8. A patient support device comprising:
   a base member;
   an upright member for a patient to gasp with said upright member pivotally carried by said base member to permit said upright member to be moved from a collapsed and out-of-the-way position to an extended position where a patient can grasp said upright member for support while an x-ray is being taken of the patient; and
   an angled patient support bar mounted thereto to project outward from said patent support device.

9. The patient device of claim 8 wherein the patient support bar is made of wood.

* * * * *